United States Patent [19]

Quackenbush

[11] Patent Number: 5,125,913
[45] Date of Patent: Jun. 30, 1992

[54] SOFT-TIPPED CATHETERS

[75] Inventor: John J. Quackenbush, Birmingham, Ala.

[73] Assignee: FBK International Corporation, Birmingham, Ala.

[21] Appl. No.: 523,053

[22] Filed: May 11, 1990

[51] Int. Cl.⁵ ............................................. A61M 5/00
[52] U.S. Cl. ...................................... 604/264; 604/93; 156/159; 156/244.18; 138/140
[58] Field of Search ............... 604/96, 264, 265, 280, 604/282, 281; 156/158, 159, 244.18, 253; 428/34.6; 138/140, 141, 145, 146

[56]   References Cited
       U.S. PATENT DOCUMENTS

| 4,627,844 | 12/1986 | Schmitt ........................ 604/264 |
| 4,755,171 | 7/1988 | Tennant ........................ 604/265 |
| 4,790,831 | 12/1988 | Skribiski ...................... 604/264 |
| 4,863,442 | 9/1989 | DeMello et al. ............... 604/282 |
| 4,886,506 | 12/1989 | Lovgren et al. ............... 604/282 |
| 4,898,591 | 2/1990 | Jang et al. .................... 604/264 |
| 4,950,257 | 8/1990 | Hibbs et al. ................... 604/264 |
| 4,994,047 | 2/1991 | Walker et al. ................. 604/264 |

FOREIGN PATENT DOCUMENTS 03323065  9/1989  European Pat. Off. ............ 604/264

Primary Examiner—C. Fred Rosenbaum
Assistant Examiner—Chalin Smith
Attorney, Agent, or Firm—Herbert M. Shapiro

[57] ABSTRACT

A double-layer medical catheter with an integral soft tip is made by the coextrusion of a relatively rigid inner layer and a relatively soft outer layer, where the extrusion equipment is configured and so controlled to interrupt the supply of the material for the inner layer to form a periodic void in the inner wall. The act of interrupting the supply causes a ramp down in the inner wall thickness at the leading edge of each void and the ramp up of the thickness at the trailing edge. The void is cut to produce two ideal integral soft-tipped catheters.

4 Claims, 3 Drawing Sheets

SOFT-TIPPED CATHETERS

FIELD OF THE INVENTION

This invention relates to medical catheters and more particularly to such catheters which have soft distal ends on tips.

BACKGROUND OF THE INVENTION

A variety of criteria have to be met for medical catheters to be serviceable. Some of these requirements are at least somewhat inconsistent with one another. For example, a catheter, in order to have the distal end follow the proximal end, has to be made of material of a rigidity to convey torque from the proximal to the distal end. Unfortunately, any material sufficiently rigid to convey the torque may be too rigid to maneuver in some areas in the body into which insertion is required. The tip has to be softer than the body of the catheter.

Prior art attempts to overcome this problem include gluing a tip of relatively soft material onto the distal end of the catheter. This approach has proven to be hazardous, because the tips do come off, and are difficult to retrieve as they move in the body. Also, if such a tip reaches the heart, it most likely is fatal.

Another attempt is to make a catheter with a relatively rigid inner layer and a relatively soft outer layer. The inner layer is removed from the distal end and the outer layer at the distal end is heated and drawn down to form a soft tip. This approach not only is relatively expensive, but reduces the thickness of the catheter wall at the tip, running the risk of rupture and sacrificing torque. Further, lumen diameter is difficult to maintain constant.

BRIEF DESCRIPTION OF AN ILLUSTRATIVE EMBODIMENT OF THIS INVENTION

The present invention is based on the recognition that an integral soft tipped catheter can be extruded in a manner to avoid the above difficulties. The invention is based on the recognition that a catheter can be fabricated in a coextrusion process where a relatively rigid inner layer of a polyamid type 11 material (i.e., 90A durometer Nylon TM) can be coextruded with a relatively soft outer layer of say 55 durometer material in an extrusion die where the supply of the inner layer material is periodically interrupted. The result is that the layer wall thickness will ramp down at the leading edge of the interruption and ramp up at the trailing edge.

A plurality of soft-tipped catheters results by cutting the output of the diffusion die in the middle of each of the periodic areas where the inner layer is missing. The soft tip which results is not only integral, but has no reduced wall thickness and can be formed at any diameter.

The diffusion die for producing the desired extrusion profile contains a means for interrupting the flow of the material for the inner wall quickly. When the interruption occurs, the pressure on the material downstream of the interruption is reduced, thus resulting in the gradual reduction in inner wall thickness at the leading edge of each of the voids in the inner wall. When the interruption terminates, the resulting increasing pressure produces a gradual increase in inner wall thickness at the trailing edge of each void.

Applicant believes that an integral soft tipped catheter having an inner and an outer wall where the inner wall has a thickness which increases with distance from the distal end of the catheter, along with the diffusion equipment of a form, and so controlled to form a continuous stream of double-walled catheter structures with periodic voids in the inner wall and the method for so forming such a catheter, represent significant departures from prior art thinking.

DETAILED DESCRIPTION OF AN ILLUSTRATIVE EMBODIMENT OF THIS INVENTION

Figure 1:
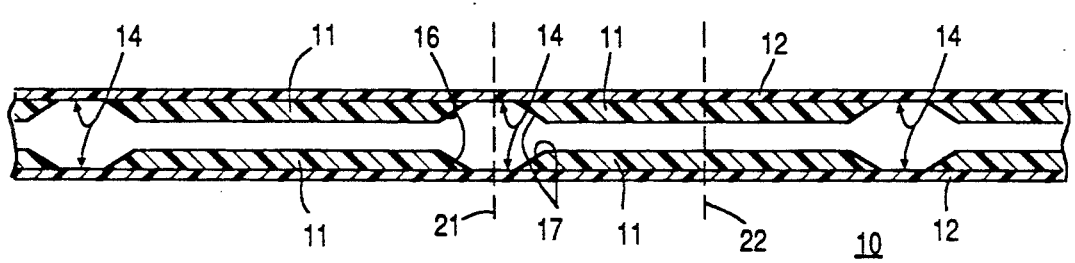
FIG. 1 is a schematic cross-section of a tube in accordance with the principles of this invention.

FIG. 1 shows a cross-section of a tube 10 in accordance with the principles of this invention useful for making catheters with integral soft tips. The tube comprises an inner layer 11 and an outer layer 12. Inner layer 11 can be seen to include voids 14 at which no inner layer material is present.

Tube 10 is formed by extrusion. If we accept the assumption that the tube is extruded from the right as viewed, it is consistent to designate the left edge of each void 14 as the "leading edge" and the right side of each void as the "trailing edge." Representative leading and trailing edge are designated 16 and 17 in the figure.

Figure 2:
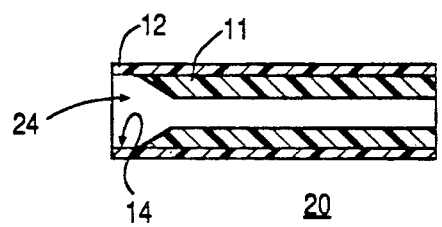
FIG. 2 is a schematic cross-section of a portion of the tube of FIG. 1.

FIG. 2 shows a portion 20 of the tube of FIG. 1 between vertical broken line 21 and 22 of FIG. 1. The portion can be seen to constitute a catheter having an integral soft tip at its left end 24 as viewed. The soft tip is formed by the extrusion of (relatively soft) outer layer 12 beyond the point in void 14 where inner layer 11 is absent. The distal end (to the right as viewed) in FIG. 2 terminates at a position where both the inner and the outer layers are at full thickness. A typical thickness for the outer and inner layers are 0.015" and 0.010" respectively. The thicknesses for such layers may range from about 0.0001" to 0.020", and from 0.002" to 0.010" for normal catheters, depending on the number of lumens present. It is contemplated to employ a soft tip with catheters having either a single or multiple lumens. The catheters can be made of any bio-compatible, FDA-approved material such as Dow 2363-55D Pellethane (a medical grade polyurethane resin) and Atochem BESNO Nylon 11 for the outer and inner layers respectively.

Figure 3:
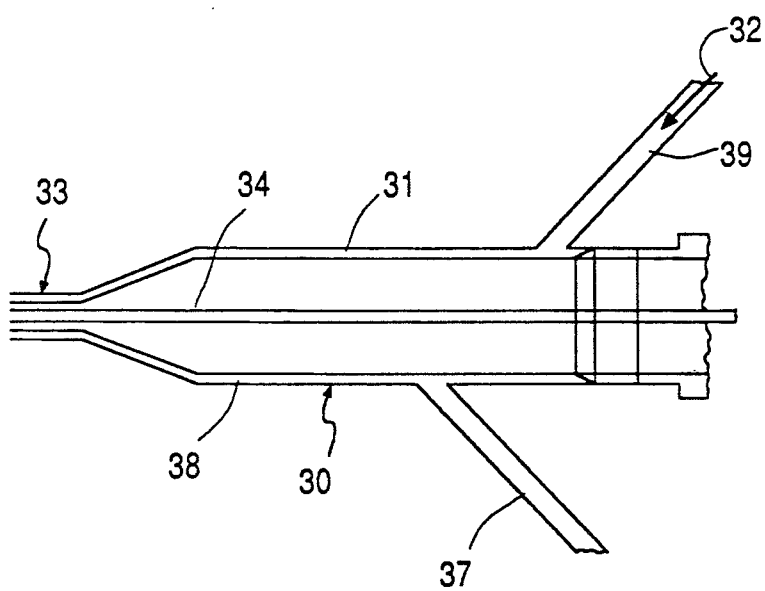
FIGS. 3, 4 and 5 are schematic plan, front and side views of an extrusion die manifold and control for forming the tube of FIG. 1.

FIG. 3 shows apparatus 30 for extruding a catheter tube having an inner and outer layer. In the illustrative embodiment, only a single lumen is provided for. Additional lumens are provided in a well-understood manner and are not discussed further.

The apparatus comprises a source of material providing a flow stream 31. The source is indicated by arrow 32. Stream 31 is fed into tubular constriction 33 to form the inner layer of a catheter. The center bore 34 of the apparatus is connected to a source of air pressure greater than normal air pressure.

The outer layer of the catheter is formed from a lower durometer material introduced via input 37. The material, so introduced, is formed into a sleeve about inner layer 11 by jacket 38, which confines the flow stream 31. The material introduced at 37 is formed into the outer layer of the catheter at 33.

The apparatus also includes a means for interrupting the flow of material 31. Such a means is located upstream of the position where the material for the outer layer is introduced (i.e., via 37). Typically, the position of the means for interrupting is located on input port 39, to the right as viewed in FIG. 3. Such a means comprises an extrusion interpolating die manifold and timer control as shown in FIGS. 4 and 5.

Figure 5:
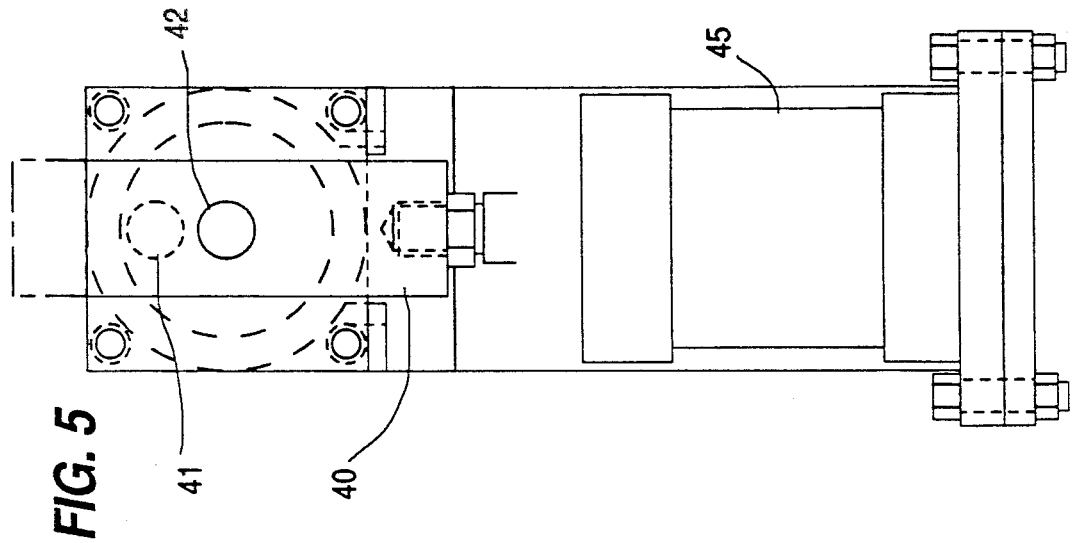
Figure 4:
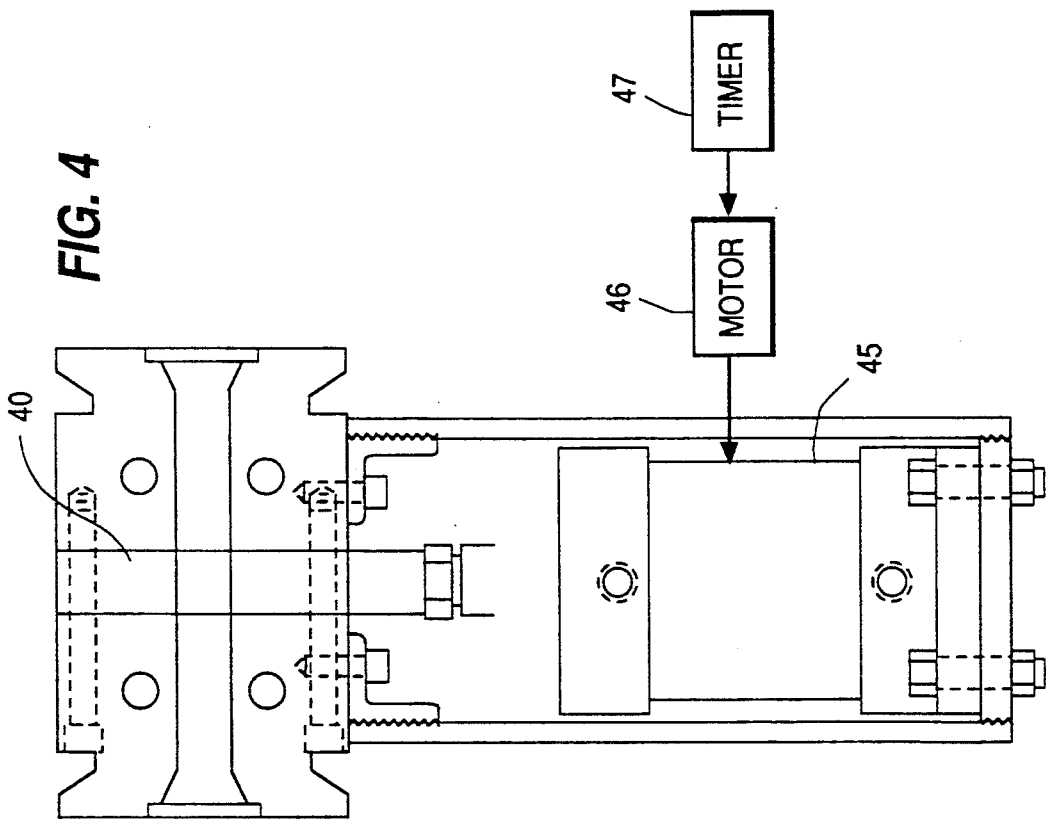

FIGS. 4 and 5 specifically show a baffle 40 which is in the path of the melt flow (31) of the material for the inner layer. The baffle includes an aperture 41 in it. The aperture has a diameter to correspond with the diameter of input port 39 for the material for the inner layer. When the aperture is in position 42 of FIG. 5, no interruption of the material supply occurs. When the aperture is moved to the position (41) shown in FIG. 5, the supply is interrupted.

The baffle is mounted on a cylinder 45 which is moved by motor 46 of FIG. 4 according to a pre-set timing regimen imposed and controlled by timer 47. The motor periodically moves the baffle from a position where the aperture corresponds to position 42 to that of position 41 and back again to create a series of voids in the inner wall of the catheter tubing as shown in FIG. 1.. The length of the void and the separation between voids is determined by the time between consecutive movements of the aperture to the "interrupt" position (viz: 41) and the time for which the aperture remains in that position. Therefore, the tube profile is entirely controlled by the timer.

The ramp profile of the inner wall thickness at the leading and trailing edge of each void is determined by the pressure at which the extrudate for the inner layer is maintained and the speed at which the baffle is moved. The ramp profile is also a function of the pressure at which the outer wall extrudate is maintained. Clearly, if the extrudate for the outer wall were not moving when interruption of the inner wall material occurred, no void would occur in the inner wall regardless of the baffle position. All these parameters are clearly controllable in conventional fashion and are arbitrary.

Figure 6:
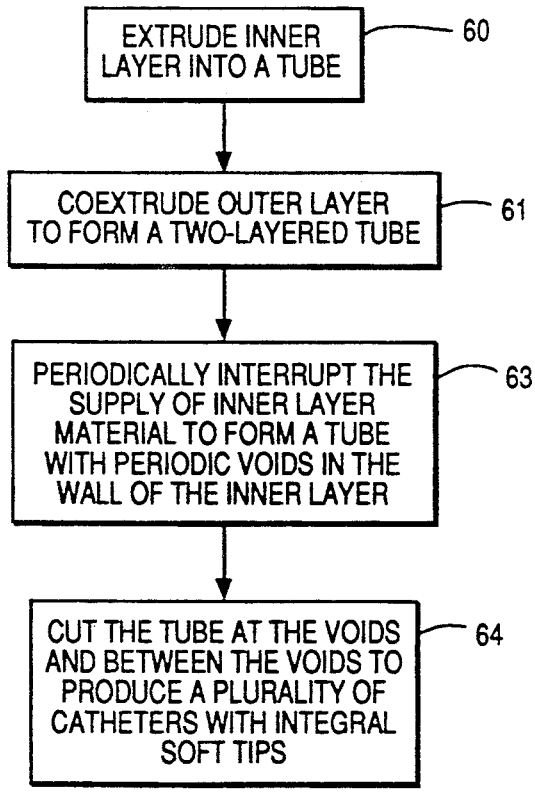
FIG. 6 is a block diagram of the method for forming the tube portions of FIG. 2.

FIG. 6 is a block diagram of the steps of a method for forming a catheter with an integral soft tip in accordance with the principles of this invention. The method comprises the steps of forming a first extrudate into a tube as indicated by block 60. The second step is to form a two-layered tube while still in the melt phase. This step is indicated by block 61.

The third step is to interrupt the flow of the first extrudate while the second extrudate is still under pressure to continue forming the outer layer. This step is represented by block 63. The flow is interrupted periodically for a time to create a series of voids in the inner wall of the advancing double-walled tube while still in the melt phase.

The final step is to cut the tube so formed in the middle of each void and between each void to make a plurality of catheters as shown in FIG. 2. This step is represented by block 64.

The end of each catheter (distal end) includes an integral soft tip formed of the material of the outer layer of the catheter only. That tip may be heated and/or extended to form a reduced diameter opening, if so desired.

What is claimed is:

1. A tube for forming a plurality of soft tip catheters comprising of a first inner wall of a relatively rigid material and a second outer wall of relatively soft material, said inner wall having a plurality of periodic voids therein, said voids being spaced apart distances which are large compared to the length of said voids, each of said voids having leading and trailing edges, the thickness of said inner wall at each of said leading edges decreasing with distance towards the associated void, the thickness of said inner wall at each of said trailing edges increasing with distance away from the associated void.

2. A tube as set forth in claim 1 wherein said inner and outer layers are made of biocompatible flexible plastics.

3. A tube as set forth in claim 1 wherein said inner layer a polyamid type 11 material.

4. A portion of a tube as set forth in claim 1, wherein the first and second walls are formed of biocompatible materials, said portion being formed by cutting said tube in the middle of a first void and between said void and the next void where said inner layer is at its full thickness, to form a catheter having distal and proximal ends, having an integral soft tip on its distal end, said distal end where the inner wall is least thick and said proximal end where the inner wall is most thick.

* * * * *